United States Patent [19]
Phillips

[11] Patent Number: 5,824,112
[45] Date of Patent: Oct. 20, 1998

[54] PROSTHETIC DEVICE INCORPORATING LOW ANKLE DESIGN

[76] Inventor: Van L. Phillips, 4702 San Jacinto Terrace, Fallbrook, Calif. 92028

[21] Appl. No.: 43,150

[22] Filed: Mar. 31, 1993

Related U.S. Application Data

[63] Continuation-in-part of Ser. No. 977,654, Nov. 17, 1992, abandoned, which is a continuation of Ser. No. 337,374, Apr. 13, 1989, Pat. No. 5,181,932, and a continuation-in-part of Ser. No. 844,898, Mar. 3, 1992, abandoned, which is a continuation of Ser. No. 585,920, Sep. 21, 1990, abandoned.

[51] Int. Cl.⁶ ....................................................... A61F 2/66
[52] U.S. Cl. ................................................. 623/52; 623/55
[58] Field of Search ............................................. 623/47–56

[56] References Cited

U.S. PATENT DOCUMENTS

| | | |
|---|---|---|
| 61,780 | 2/1867 | Watson .................................. 623/53 X |
| 4,547,913 | 10/1985 | Phillips . |
| 4,645,509 | 2/1987 | Poggi et al. . |
| 4,822,363 | 4/1989 | Phillips . |
| 4,938,776 | 7/1990 | Massinter . |
| 4,959,073 | 9/1990 | Merlette . |
| 4,994,086 | 2/1991 | Edwards . |
| 5,037,444 | 8/1991 | Phillips . |
| 5,062,859 | 11/1991 | Naeder . |
| 5,156,631 | 10/1992 | Merlette . |
| 5,156,632 | 10/1992 | Wellershaus . |
| 5,181,932 | 1/1993 | Phillips . |
| 5,181,933 | 1/1993 | Phillips . |

FOREIGN PATENT DOCUMENTS

| | | |
|---|---|---|
| 2626463 | 8/1989 | France ........................................ 623/55 |
| 325171 | 9/1920 | Germany . |
| 963849 | 5/1957 | Germany . |
| 778732 | 12/1980 | U.S.S.R. . |
| 806023 | 2/1981 | U.S.S.R. . |
| 2253148 | 9/1992 | United Kingdom . |

*Primary Examiner*—David H. Willse
*Attorney, Agent, or Firm*—Knobbe, Martens, Olson & Bear LLP

[57] ABSTRACT

The present invention relates to a prosthesis having a substantially rigid leg member, wherein most of the bending takes place about a confined ankle region relatively low to the ground, and in a flexible toe and ankle section, wherein the bending of the prosthesis more closely resembles the bending of a normal ankle joint. The confined bending helps to reduce the amount of horizontal deflection caused along the ankle section by the upward deflection of the prosthesis. The present invention also comprises a tubular leg member that is detachable from the ankle and foot member, and a heel member extending rearwardly from the foot member which is also detachable therefrom.

15 Claims, 7 Drawing Sheets

PROSTHETIC DEVICE INCORPORATING LOW ANKLE DESIGN

This is a continuation-in-part of U.S. application Ser. No. 07/977,654, filed Nov. 17, 1992, now abandoned, which is a continuation of U.S. application Ser. No. 07/337,374, filed Apr. 13, 1989, now U.S. Pat. No. 5,181,932. This is also a continuation-in-part of U.S. application Ser. No. 07/844,898, filed Mar. 3, 1992, now abandoned, which is a continuation of U.S. application Ser. No. 07/585,920, filed Sep. 21, 1990, now abandoned.

FIELD OF THE INVENTION

The present invention relates to prosthetic devices, and in particular, prosthetic devices incorporating a rigid shin portion and a small radius or tight ankle section.

BACKGROUND OF THE INVENTION

Many types of prosthetic devices have been developed over the years. In the early years, emphasis was placed on constructing an artificial limb which looked and moved much like a human limb. For example, many prosthetic devices were fabricated with a leg member and a foot member, with some form of pivoting member therebetween near the ankle region to allow the foot member to rotate about the ankle region. Elaborately constructed prosthetic devices were introduced, each attempting to simulate the natural movement of the human leg, ankle and foot. Though each of these attempts were intended to provide some level of normalcy to the artificial limb, they lacked the resilient energetic response needed for non-sedentary activities.

Various improvements have been made to prosthetic devices to enable the amputee to substantially increase his or her activity level. The advent of new materials, such as graphite composite materials, which are lightweight, strong, durable and relatively flexible, have been developed to further improve the performance of prosthetic devices. Also, contrary to earlier thinking, better compliance and energy response has been obtained by simplifying the structure of the prosthetic device rather than making it more complex. Prosthetic devices incorporating simple curved, flat, spring-like members have been developed which now enable amputees to participate in strenuous activities, such as tennis, basketball and jogging.

In particular, a prosthetic foot and leg device allowing a high degree of mobility on the part of an amputee was disclosed in applicant's U.S. Pat. No. 4,457,913 entitled "COMPOSITE PROSTHETIC FOOT AND LEG." That patent discloses a prosthetic foot and leg device utilizing a resin impregnated high-strength filament structure for the leg portion, foot portion and heel portion, with all three regions being provided with substantial elastic flexibility, of relatively low energy absorption characteristics, so as to give the wearer high mobility with a relatively natural feel. Contrary to earlier prosthetic devices which incorporated a rotatable or articulated ankle mechanism, this prosthetic device has no moving parts other than the inherent flexibility and energy response characteristics of the material itself.

That prosthetic device also has a substantially elastic leg portion, wherein the flexibility of the leg portion is in addition to the flexibility of the heel and foot portions. Though this flexibility provides additional energy storage and release, and gives the prosthesis increased resiliency and energy response, this additional flexibility in the leg makes the prosthesis somewhat springy, unlike the tibia and fibula of the human limb which are not flexible and elastic.

In U.S. Pat. No. 4,822,363, the applicant attempted to provide some rigidity to the shin portion so that the flexure would take place beneath the upper leg portion. However, as with the prosthetic device of the above-referenced patent, the flexibility and resiliency of the prosthetic device was built into the entire lower leg region, including the shin, foot, and heel portions, up to and including the bottom ten inches of the prosthetic device. It was thought that if the flexibility in the lower leg region was eliminated to any greater extent, the prosthesis would lose a valuable portion of its capacity to store and release energy. With at least ten inches of clearance between the lower extremity of the rigid shin portion and the ground, the curvature of the flexible shin and ankle regions was smooth and continuous, and the resiliency and energy response characteristics of this prior device was excellent, without stops or jolts during use. Furthermore, from a structural point of view, the smooth curvature of the shin and ankle regions could be adapted to have a substantial radius, thereby avoiding any stress concentrations in the prosthesis. Due to the gradual curve of a relatively large radius (in some cases the curve was complex and not a simple curve), the space beneath the curve member provided for a relatively long heel capable of demonstrating good resiliency and flexibility.

Nevertheless, the energy response of such previous devices was often too great for some patients, exceeding their particular needs. With certain geriatric or youth patients, the springiness of such prior devices was somewhat difficult to manipulate or control, reducing stability. Thus, there remains a need for a foot prosthesis which demonstrates good performance capabilities under a wide range of physical activities, but which at the same time provides enhanced safety, security, and control for the wearer.

SUMMARY OF THE INVENTION

The present invention represents a substantial improvement over the prior art prosthetic devices in that the high energy response characteristics are utilized in conjunction with a relatively stiff leg or shin portion, a lower bending axis and a tighter ankle section, which together more closely function like the ankle region of a natural human limb. Unlike the previous prosthetic devices, which flex along a relatively long leg distance, the present invention relates to a prosthetic device having an ankle section with a relatively tight radius of curvature, which substantially concentrates the bending in the ankle region to proximate the bending of the human ankle. The smaller radius of curvature also helps lower the flexing point, i.e., the axis of bending, of the prosthetic device, to more closely match the location of the human ankle region.

A lower axis of bending is an important advantage in the present invention due to the trend in recent years regarding the manner in which amputations are conducted. The medical profession is now recognizing the advantage of performing amputations lower to the ground, preserving a substantially longer stump for the amputee than in the previous conditions. This longer stump provides, in turn, a longer lever arm for use in connection with the prosthesis, thereby permitting the exertion of greater strength upon the prosthesis. This means that the prosthesis, if correctly engineered as in the present invention, can return an extremely high percentage of energy to the wearer in order to provide excellent performance; however, at the same time, the performance characteristics of the prosthesis must be accomplished in a structure which is provided with less distance from the ground to the stump. Thus, with lower amputations, higher performance is possible, but a greater risk of breakage due to stress concentrations exists.

However, the prosthesis of the present invention takes advantage of this tendency, while at the same time adequately addressing the issues of strength and performance. Thus, the present prosthesis can be used with excellent results by a much wider diversity of amputees including those with lower amputations. At the same time, stability and control are achieved.

Unlike prior art devices which disclose a flexible leg portion and a substantially large radius of curvature ankle section, which results in a very high rate of energy return, the present invention serves to relocate and confine the bending. In other words, with prior devices, flexibility and energy return were available in the upper leg regions of the prosthesis. In the present invention, however, since the upper leg region is substantially rigid, a portion of that flexibility previously available has been relocated to a newly designed ankle in which the flexibility is isolated or concentrated. While some overall performance is thereby sacrificed, greater prosthetic stability and control are achieved with yet excellent performance characteristics. This performance is also achieved through the design of cooperating heel and toe sections which have optimal flexible lever arms, as explained below in more detail. Thus, the flexibility of the present heel section upon heel strike and that of the present toe section at toe off, cooperate with the bending concentrated in the ankle region to provide a high performance prosthetic device.

In addition, in previous devices, a flexible leg portion and a relatively large radius of curvature ankle section caused the prosthesis to shift substantially in the fore and aft direction when deflected and allowed twisting in the torsional direction, which made the prosthetic device more difficult to control. Not only did amputees have to adjust to this difference, some amputees, such as geriatrics or children, lacking sufficient strength, did not have the ability to make that adjustment. The present invention addresses this problem by providing a flexible ankle section having a relatively small radius of curvature, whereby horizontal deflection is minimized. This design allows the present invention to exhibit good qualities for stability and control.

The configuration of the present invention also enhances stability and control by providing a substantially more lifelike feel. Because the present invention utilizes a substantially rigid pylon, and the bending previously available from the upper leg region is concentrated primarily in the ankle region, the additional springiness associated with the flexible leg and shin portion is eliminated. Thus, the present prosthesis flexes in the ankle region in a manner that more closely resembles the movement of the natural human limb, thereby giving the wearer better control and "feel."

More specifically, the present invention comprises a substantially rigid tubular pylon member extending downward from the stump of the amputee. Because the pylon member is substantially rigid, it performs much like the tibia and fibula of the human leg. In a preferred embodiment, the rigid pylon member is tubular and hollow to impart less weight, while providing rigidity against bending. Attached at the lower end of the rigid pylon member is a flexible ankle section which incorporates a simple curved, flat, spring-like surface, which is similar to a leaf spring. The ankle section extends downward from a vertically oriented upper section and forward to a horizontally oriented lower toe section. The curvature along the ankle section can be simple arc of a circle or a complex configuration.

The cross-sectional shape of the ankle section is preferably rectangular, although the edges do not necessarily have to be rectilinear. In the preferred embodiment, the width of the cross section of the ankle section is substantially greater than its thickness. To permit flexibility along a vertical plane in the fore and aft direction, the moment of inertia of the ankle section is relatively small about a horizontal axis perpendicular to the fore and aft direction. To restrict bending in the other planes, the ankle section has a high moment of inertia about an axis generally aligned with the fore and aft direction.

Another important advantage of the present invention is that it provides adjustability to the wearer with respect to the energy return characteristics of the ankle. Since the ankle is detachably mounted to the distal end of the rigid pylon member, it can be interchanged with ankle sections of similar design but which have different flex characteristics, thereby allowing the wearer to achieve optimal performance in connection with a wide variety of strenuous or less strenuous physical activities. Likewise, the heel section is also demountably attached to the underside of the ankle section to permit adjustability in connection with the spring rate of that element.

The substantially rigid pylon member is also interchangeable, and can be cut and adapted to different lengths. This advantageously permits the pylon member to be removed and adjusted to suit the particular size of an amputee or can accommodate a growing amputee. This permits the remainder of the prosthesis to be produced in standard sizes, while permitting pylon members to be cut and fit to the particular needs of an amputee. Applicant's invention permits prosthetists to cut a standard tubular or other relatively stiff pylon to an appropriate length, eliminating the risk that the more expensive prosthesis having an integral leg section might inadvertently be cut too short. This also reduces the amount of material needed to produce the prosthesis, eliminates the waste attributed to cutting the extra length of leg section, makes the prosthesis lighter, and substantially lowers the cost.

In summary, the present prosthesis provides good performance characteristics while enhancing stability and control for the wearer. In addition, the prosthesis, due to its simple design, can be inexpensively manufactured as compared to previous prosthesis.

BRIEF DESCRIPTION OF THE DRAWINGS

FIG. 9b is a schematic drawing showing the set up of the test shown in FIG. 9a.

DESCRIPTION OF THE PREFERRED EMBODIMENTS

The present invention relates to a prosthetic device utilizing a relatively stiff leg or shin portion and a substantially small radius ankle section, which together serve to confine the point of bending to more closely simulate the dorsiflexion and plantarflexion of the natural human foot at the ankle joint. It should be noted that when the term "radius" or "radius of curvature" is used herein, it is not intended to be limited to a simple arc or curve, but is intended that complex curves are also within the scope of the present invention. For convenience, these terms are used to simplify the description; however, one of ordinary skill in the art will understand that non-simple curves are equally feasible.

In particular, the present invention has a relatively stiff shin portion, in combination with a flexible ankle section having a tight radius of curvature, which helps lower the flexing point of the prosthetic device. This combination also isolates the point of bending so that the bending axis is more closely in line with the center line of the load on the prosthetic device.

Construction of the Prosthesis

Figure 1:
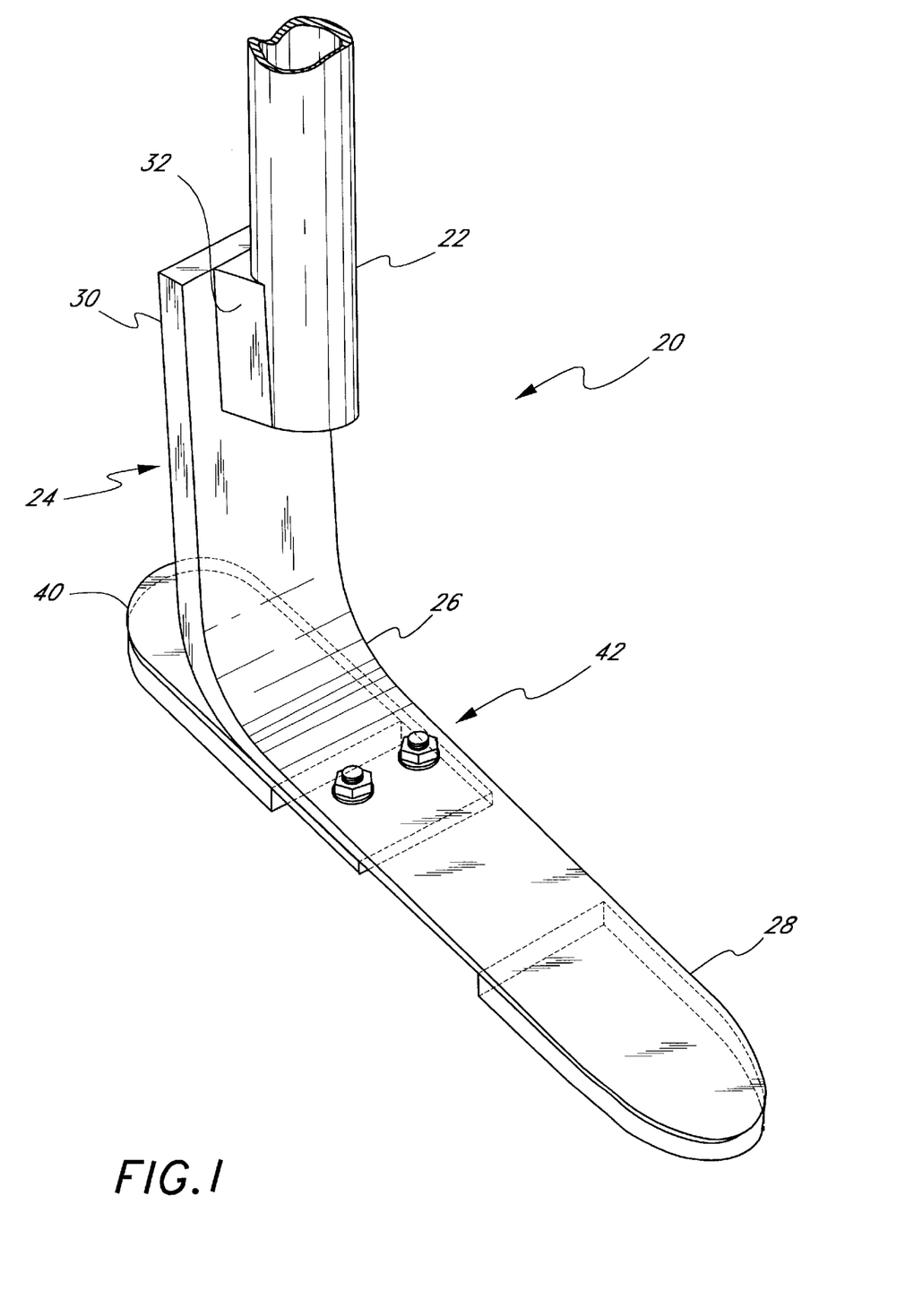
FIG. 1 is a perspective view showing the prosthetic device of the present invention with a pylon connected.
Figure 2:
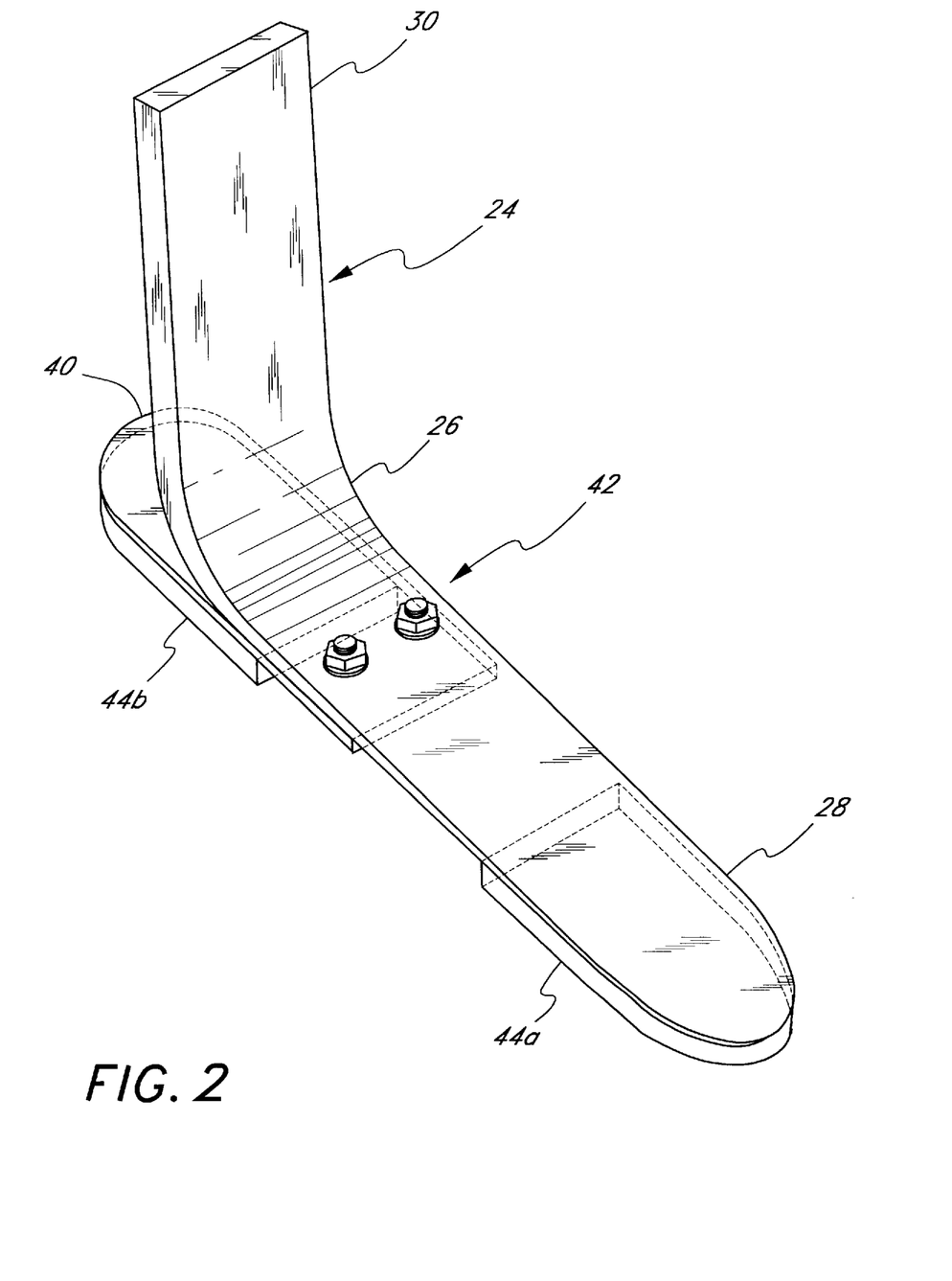
FIG. 2 is a prosthetic device similar to FIG. 1, without a pylon.

As can be seen in FIG. 1, the prosthesis 20 of the present invention has a pylon member 22 which can be secured to the stump of the amputee (not shown) and extends relatively downward therefrom in a generally vertical direction. The pylon member 22 in the preferred embodiment is of tubular construction, having an equal moment of inertia in all directions to restrict bending in all directions. The tubular member 22 is also hollow so that it is relatively light in weight, and utilizes less material, which reduces the cost of production, and preferably has the dimensions of standard tubular pylons.

Other configurations which impart rigidity, such as rectilinear cross sections having relatively larger moments of inertia, can also be utilized to obtain the benefits discussed herein. Stiffness in the pylon member 22 can also be provided by a stiffer and more dense material.

The tubular pylon member 22 can also be removed from the prosthetic device, such that the pylon member can be replaced without replacing the remainder of the prosthetic device. This permits applicant's invention to be utilized in a broader range of applications.

For instance, the tubular member 22 of applicant's invention can be cut and adapted for use by amputees having different stump lengths, including growing amputees. The prosthetist merely needs to cut a standard tubular pylon to the appropriate length. Moreover, this eliminates the need to manufacture, as a part of the prosthesis, a long rigid leg section. Thus, fewer materials are needed to manufacture the prosthesis of applicant's invention, resulting in reduced manufacturing costs.

As shown in FIG. 1, a foot portion 24 is secured to the pylon member 22 such that the foot portion extends downward therefrom. In the preferred embodiment, the foot portion 24 is comprised of an elongated member having a relatively flat, curved surface and a rectilinear cross section made of substantially flexible and durable material. Also, the foot portion 24 can be made of non-rectilinear cross-sections to achieve the same benefits discussed herein. As can be seen in FIG. 1, the foot portion 24 in the preferred embodiment extends generally vertically downward from the pylon member 22, bending about an ankle region 26 and extending to a toe section 28.

In the preferred embodiment, the thickness of the foot portion 24 is a small fraction of its width, whereby the moment of inertia about a horizontal axis perpendicular to the fore and aft direction is substantially smaller than the moment of inertia about a horizontal axis generally in the fore and aft direction. This configuration permits bending in a vertical plane in the fore and aft direction, while restricting bending about other planes. The configuration also helps to control torsional movement by allowing some, but prohibiting excessive, movement.

Figure 3:
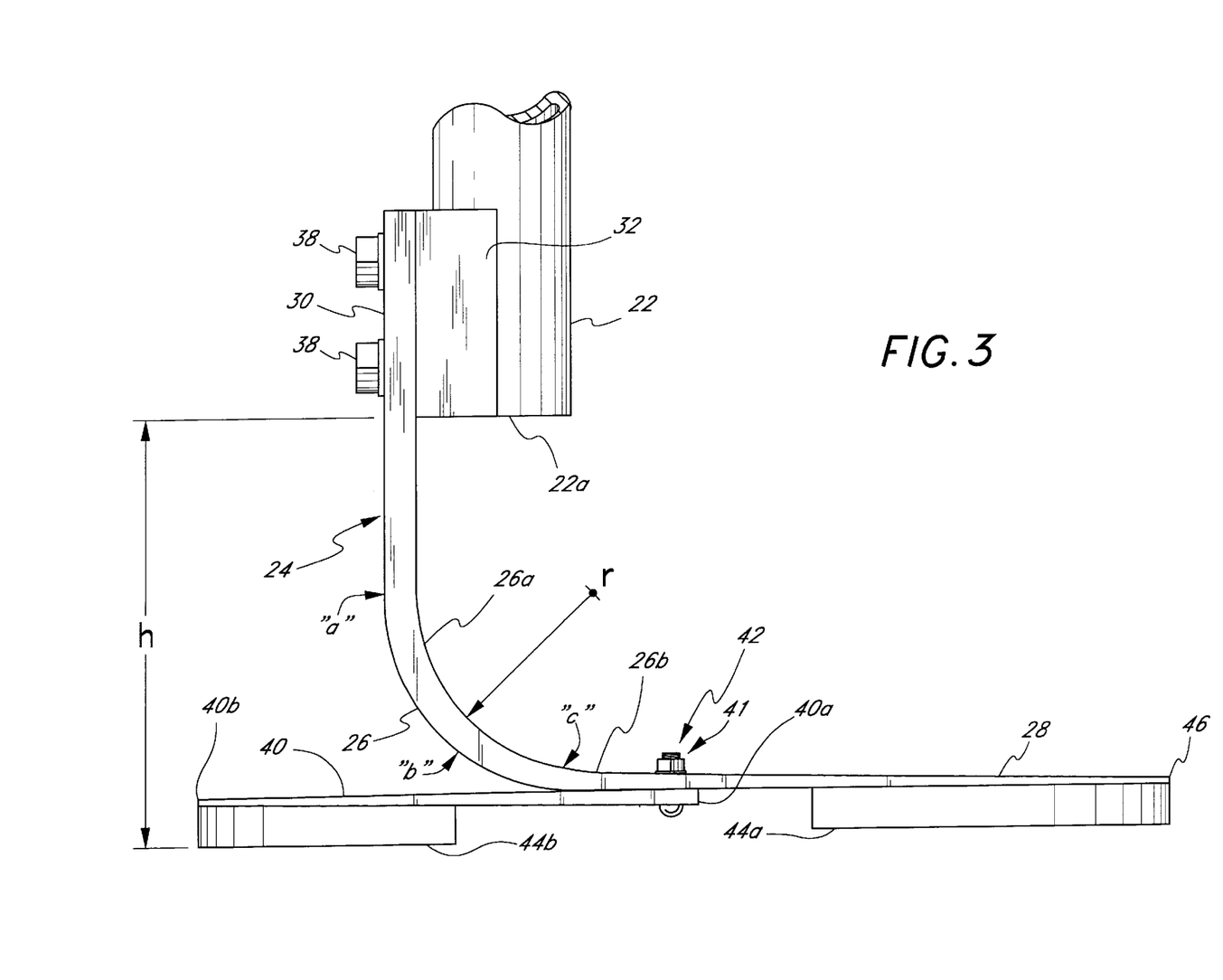
FIG. 3 is a side elevational view of the prosthetic device of FIG. 1.
Figures 4, 5:
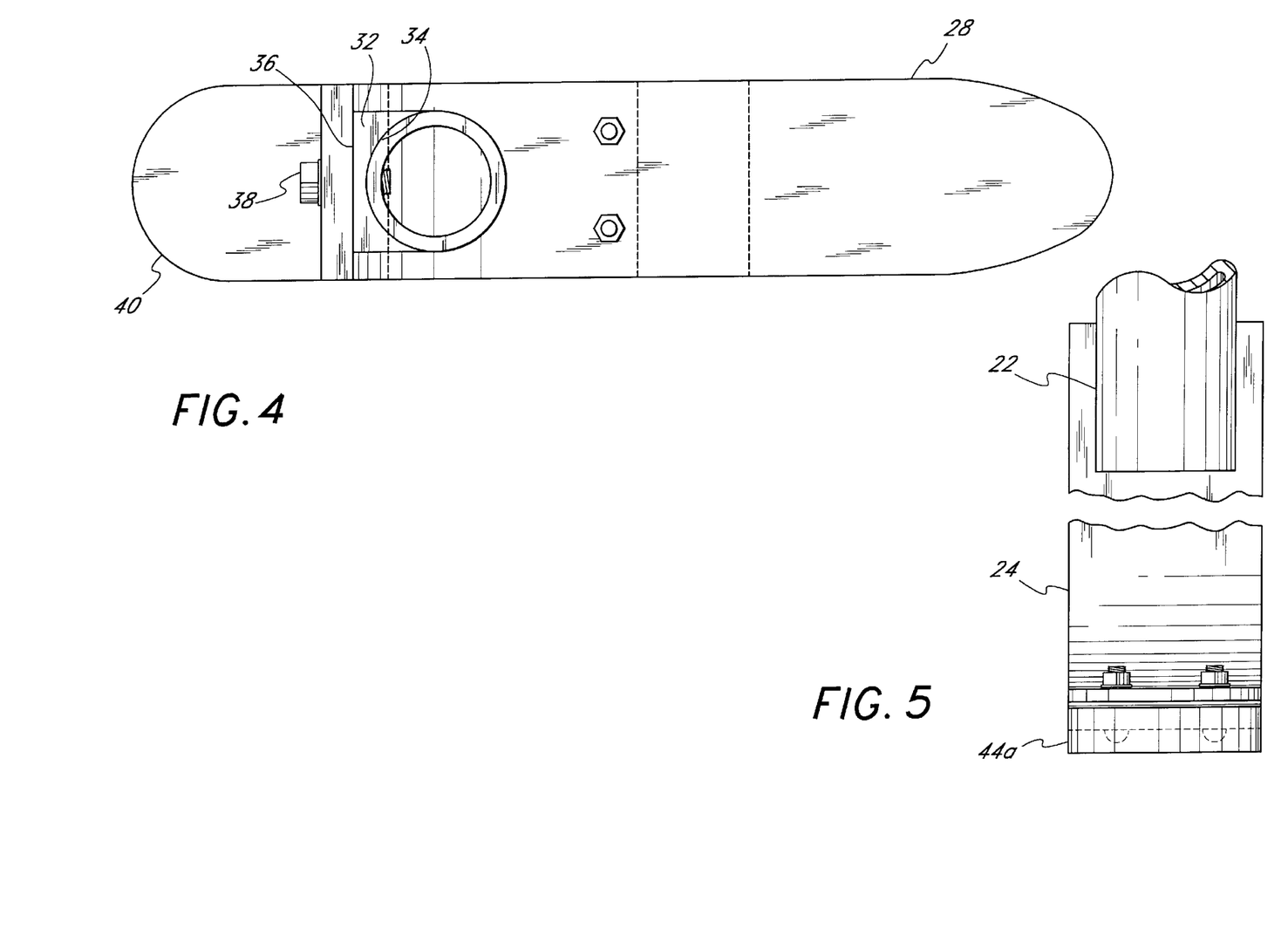
FIG. 4 is a top plan view of the prosthetic device of FIG. 1.
FIG. 5 is a front elevational view of the prosthetic device of FIG. 1, with a portion of the middle ankle section middle removed.

With reference to FIGS. 1, 3 and 4, the upper section 30 of the foot portion is, in the preferred embodiment, vertically oriented so that it may be secured to the pylon member 22, as seen in FIG. 1. As shown in FIG. 3, an attachment device 32 is positioned at the lower end of the pylon member 22, which provides a flat surface upon which the vertical section 30 of the foot portion 24 can be secured. The attachment device has one attachment surface 34 which mates with the outside surface of the pylon member 22, and a second attachment surface 36 which mates with the foot portion 24. In the preferred embodiment, one attachment surface 34 of the attachment device is curved to mate with the outside surface of the tubular pylon member 22, and the second attachment surface 36 is flat to accommodate the flat upper section of the foot portion.

Desirably, the attachment device 32 is welded to the pylon member 22 and has two holes (not shown) into which two bolts 38 can be inserted and secured. The upper section 30 of the foot portion 24 also has two holes (not shown) which align with the two holes on the attachment device 32, such that by placing and securing two bolts 38 through the foot portion and the attachment device, the foot portion can be secured to the lower end of the pylon member. Other methods of securing the pylon member to the foot portion are contemplated, such as those disclosed in my copending application Ser. No. 07/856,666, filed Mar. 24, 1992, as well as those utilizing integrally formed constructions.

As shown in FIG. 3, the ankle portion 26 is demountably attached to the pylon 22 by means of fasteners 38 and demountably attached to the heel 40 at the forward connection 42 by means of fasteners 41. Thus, as noted above, the ankle portion 26, as well as the heel portion 40, are interchangeable with other similar portions in order to achieve prosthetic adjustability.

As stated, the upper section 30 of the foot portion 24 is vertically aligned so that it extends relatively downward from the attachment device 32 on the pylon member 22. As shown in FIG. 3, thickness of the foot portion 24 along this vertical section is relatively greater than the thickness of the foot portion along the toe section 28. This thickness provides sufficient rigidity to the connection between the pylon member 22 and the foot portion 24. This upper section 30 is also made relatively thicker to support the vertical load imposed on the prosthetic device 20, as well as restrict undue bending at this juncture. The entire upper vertically aligned section 30 is of uniform thickness and width.

In the preferred embodiment, as shown in FIG. 4, the foot portion 24 is a substantially constant width from the upper rigid portion 30 down to the toe section 28, with the toe end 46 being rounded to accommodate various cosmesis which simulate an actual foot. Desirably, the foot portion 24 has a width of between 1½ and 3 inches, and the width is preferably about 2 inches. Of course, one of ordinary skill will immediately recognize that prosthetic feet having different dimensions and parameters can achieve the advantages of the present invention, and that the dimensions and parameters provided herein are merely only one example of an embodiment of the present invention.

Referring again to FIG. 3, attached to the foot portion 24 is a heel portion 40, which is secured to the underside of the foot portion 24 between the ankle region 26 and the toe section 28. The heel portion 40 is also relatively flat, although it can be curved. It also has a rectilinear cross section in the preferred embodiment, although in other embodiments the cross section does not necessarily have to be rectilinear. The heel portion 40 is also made of the same flexible and durable material as the foot portion 24, as will be discussed, and has a thickness which is a small fraction of its width. Thus, its bending characteristics are similar to the bending characteristics of the ankle section.

The heel portion 40 extends rearward from a forward connection 42 with the foot portion 24, and has a length, in the preferred embodiment, which is greater than its width. The configuration of the heel portion 40 is designed to be relatively flexible about an axis parallel to its width, while being resistant to flexing about an axis parallel to its length and about an axis normal to the surface of the heel portion.

In order to provide a uniform walking surface on the underside of the prosthetic device 20, one or two separate sole members 44a and 44b are included in the present invention, as shown in FIG. 3. A front sole member 44a is adhesively attached to the underside of the toe section 28 of the foot portion 24, and a rear sole member 44b is adhered to the underside of the heel portion 40. The sole members 44a,b may be constructed from a similar material as the foot and heel portions 24, 40, or may be manufactured from a more pliant material such as urethane or a hardened rubber.

The present invention is made of a resin impregnated, high strength material, such as graphite composite, or a filament structure, arranged in laminates. Excellent results have been obtained using carbon filament with an epoxy binder, such as those disclosed in my previous U.S. patents, Pat. Nos. 4,547,913 and 4,822,363, the relevant portions of which are incorporated herein by reference. In particular, the foot portion 24 and heel portions 40 of the present invention are made of a resin impregnated, high strength material having substantially elastic flexibility so as to impart relatively low energy absorption to give the wearer high mobility and a relatively natural feel.

The rigid pylon member 22 can also be made of the same material. The pylon member's rigidity, however, is provided predominantly by its tubular shape. But because the material has some elastic flexibility, in spite of the tubular shape, the pylon member 22 has some nominal flexibility. The components of the present invention, however, are not limited to construction from such a material, but rather can be made of materials with such characteristics.

The present invention can also be integrally formed, rather than modularly formed, although in the preferred embodiment, the pylon member 22 is removable from the foot portion 24, and the heel portion 40 is removable from the foot portion. This modularity is provided by a nut-and-bolt construction, similar to the construction disclosed in my previous application Ser. No. 07/337,374.

Curvature of the Ankle Section

To impart the benefits of the present invention, and to isolate the bending of the foot portion 24, thereby approximating the dorsiflexion and plantarflexion of the human ankle region, the foot portion is provided with a tightly curved ankle section 26, curving downward and forward to the toe section 28 which is at approximately a 90° angle with the vertically aligned upper section 30. The radius of curvature "r" (shown in FIG. 3) at this ankle section 26 is, in the preferred embodiment, approximately 2 inches, with a desirable range being between ½ inch to 3 inches. Though in the preferred embodiment this curvature follows a simple arc having a relatively constant radius, the curvature can also follow a complex arc having a varying radius of curvature, such as shown in my previous application Ser. No. 07/337,374, which is incorporated herein by reference. This tight radius of curvature, in conjunction with the relatively stiff pylon member 22 and the relatively thick upper section 30 of the foot portion 24, locates the axis of bending lower to the ground and more closely resembles the position of the human ankle region. In addition, as noted above, a lower axis of bending permits the present prosthesis to be mounted on a longer stump, as exhibited by the present trend toward lower amputations. Although this configuration concentrates the flexibility and corresponding bending stresses in the ankle region 26, the present ankle has been designed, as explained below in more detail in connection with Table 1, so as to return good performance characteristics while adequately resisting such bending stresses.

In the preferred embodiment, the foot portion 24 is secured to the back side of the pylon member 22, as can be seen in FIG. 3. This off-center alignment advantageously helps to position the axis of bending closer in line with the center line of any vertical loads imposed on the prosthetic device. This tends to reduce moment forces when the foot is subjected to such vertical loads, and further reduces any horizontal deflection when the toe is subjected to vertical loads, as explained below in more detail. This off-center rearward alignment also increases the toe lever arm to provide additional leverage, which assists in providing flex balance. As can be seen in FIG. 3, the radius of curvature "r" of the ankle section 26 has a center axis which is substantially below the lower end 22a of the pylon member 22, and therefore closer in line with the vertical centerline of the pylon.

This configuration lowers and isolates the bending of the foot portion 24, while permitting additional flexibility and energy storage and release in the foot portion. A longer foot portion tends to be more flexible and therefore provide more energy storage and release. By connecting the foot portion 24 on the back side of the pylon member 22, the foot portion extends upward above the lowest extremity 22a of the pylon member, imparting additional flexibility while still confining and lowering the bending axis.

By attaching the foot portion 24 to the back side of the pylon member 22, the lever arm of the toe section 28 is extended, thereby providing additional toe flexibility and foot portion leverage. The foot portion 24 extends downward from the back side of the pylon 22 and extends forward, thereby providing a greater moment arm relative to the bending axis of the ankle section 26. This additional leverage provides the amputee with better control during the toe off phase of a normal stride. Though the foot portion 24 can also be attached to the front side of a pylon member, the lever arm of the toe section 28 would be reduced, thereby permitting less resiliency and energy response in the forward section of the prosthesis.

It should be noted that many parameters must be considered in designing a high performing foot prosthesis of this type. The principal design parameters are: (1) the point of attachment of the prosthesis to a relatively rigid upper pylon; (2) the flex characteristics of the ankle member, as determined primarily by its radius of curvature and thickness; (3) the toe length and flex characteristics of the toe member; and (4) the heel length and flex characteristics of the heel member. Other factors, such as overall weight and cosmetic compatibility, must be considered, but these are the more important performance parameters.

In addition, it will be readily recognized that these parameters represent a number of compromises or tradeoffs. For example, as noted herein, if the point of attachment of the foot prosthesis is relatively low, the ankle section of the present design exhibits a relatively tight radius, thus restricting maximum energy response. The ankle, however, exhibits good energy response with some restricted vertical deflection (or reduced "springiness" as described herein), providing greater control and stability. At the same time, the curvature of the ankle must be thickened, as explained below in more detail, to accommodate the concentration of bending stresses therein. In addition, the curvature of the ankle must provide sufficient clearance from the ground to accommodate a heel of adequate length. Thus, a number of tradeoffs have been considered in arriving at the optimal design of the present invention.

The ankle design of the present invention also permits an optimal toe and heel configuration to cooperate in the overall performance of the foot prosthesis. In one particular example, a prosthesis manufactured in accordance with the present invention and having a radius of curvature "r" of about 2 inches cooperated with a toe lever arm as measured from the forward point of attachment 42 to the tip of the toe 46 of about 4½ inches, while the cooperating heel lever arm from the same point of attachment to the distal tip of the heel 40 is about 4½ inches. Although many other prostheses of different dimensions are within the scope of the present invention, it is believed that the present invention provides optimization of performance characteristics with safety and low cost.

Though the preferred embodiment has a separate foot portion 24 secured to a separate pylon member 22, the present invention also contemplates a foot portion that is an integral extension of the pylon member, such that the axis of the pylon member is in line with the axis of the upper section 30 of the foot portion. Though some prior devices have a similar configuration, wherein a flexible foot portion extends downward from a rigid upper section, none of the prior devices particularly disclose the tight radius of curvature ankle section 26 and the low bending axis described herein.

In the preferred embodiment, the pylon member 22 has a lower extremity 22a which extends to about three and one-half inches from the bottom of the sole members 44a,b. Though this distance "h", as shown in FIG. 3, can be adjusted to accommodate various amputee preferences, including size, weight, resiliency, springiness, flexibility and activity level, the advantages discussed herein are readily obtained if the lower extremity 22a of the pylon member 22 extends no more than about five inches and no less than about two and one-half inches from the bottom of the sole members 44a,b, with a range between two and one-half to five inches.

The exact location of the pylon member 22 with respect to the foot portion 24 is determined by a combination of factors, including the length, thickness and curvature of the foot portion. The closer the lower extremity of the pylon 22 is to the bottom of the sole members 44a,b, the tighter the radius of curvature of the ankle section 26 must be. Concurrently, the tighter the radius, the thicker the ankle section 26 must be because stress concentrations become more isolated. Even though the increased thickness of the ankle section 26 causes it to become more rigid, substantial flexibility of the ankle section can still be achieved by a high performance ankle section.

Because the thickness of the ankle section 26 slightly lowers the resiliency and energy response provided by the prosthetic device 20, the present invention is well adapted for use by those who are moderately active and who are willing to sacrifice a small degree of maximum performance in exchange for greater stability and control. In addition, because the prosthetic device 20 achieves a movement and performance that resembles a human limb, it is ideal for active use, such as in running, jogging and jumping.

Figures 6, 7:
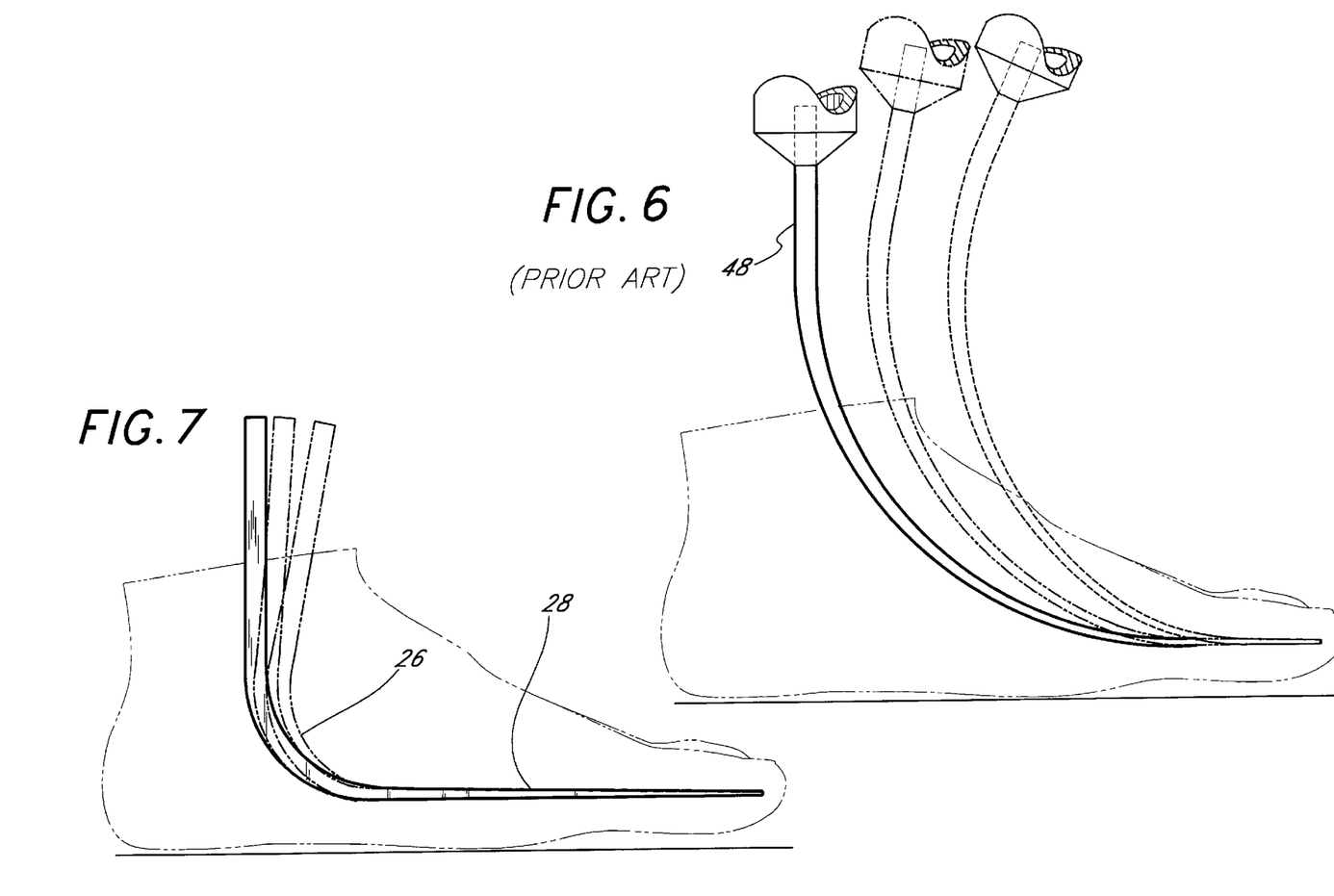
FIG. 6 is a schematic diagram showing the flexing and movement of a prior art prosthetic device.
FIG. 7 is a schematic diagram showing the flexing and movement of the prosthetic device of the present invention.

Concentration of Bending at the Ankle Section and Reduction of Horizontal Deflection One advantage of the present invention is the manner in which the prosthesis bends or deflects. FIGS. 6 and 7 provide a comparison of the way the prosthesis of the prior art bends with respect to the way the prosthesis of the present invention bends. As can be readily seen, the prosthesis of the prior art has a wide range of movement through the length of the flexible prosthetic leg and ankle member. The bending, and therefore deflection, occurs along the entire length of the flexible member. On the other hand, the flexible member of the present invention tends to concentrate bending near the curved ankle section 26, although in a normal gait, additional deflection will occur along the toe section 28. FIGS. 6 and 7 are intended to show the deflection of the curved portion of the flexing member, i.e., the ankle section.

An important aspect of the present invention is the concentration of bending, which is accomplished by reducing the radius of curvature of the ankle section 26. With previous devices, a relatively long flexing member was provided so that greater amounts of energy could be stored along the length of the flexing member. The goal was to obtain as much performance from the bending and deflection which occur throughout the length of the flexing member.

However, prior devices having relatively long flexing members, and large radius ankle sections, tended to be overly springy, deflecting substantially in the fore and aft direction. Indeed, one of the important benefits of the present invention is a reduction in the horizontal movement caused by the flexing of the ankle section.

Figure 8A:
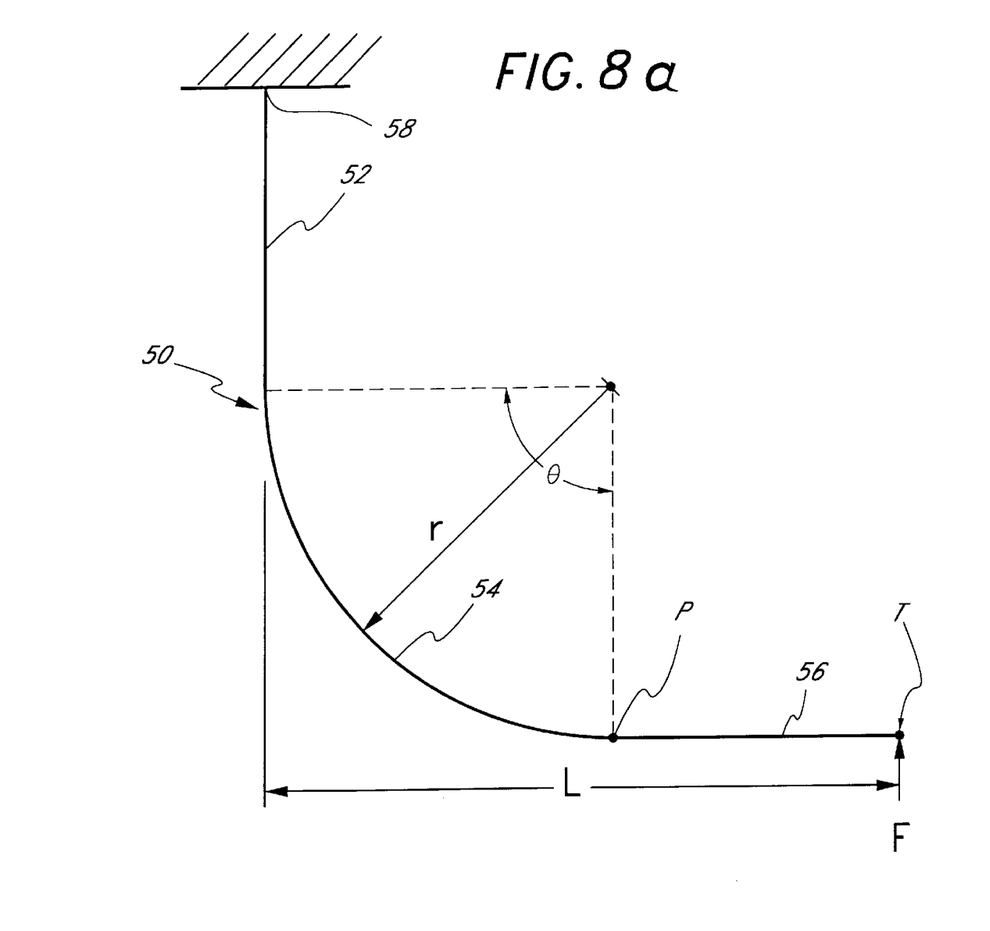
FIG. 8a is a schematic showing an idealized representation of a prosthetic ankle having a load applied upwardly at the toe region.
Figure 8B:
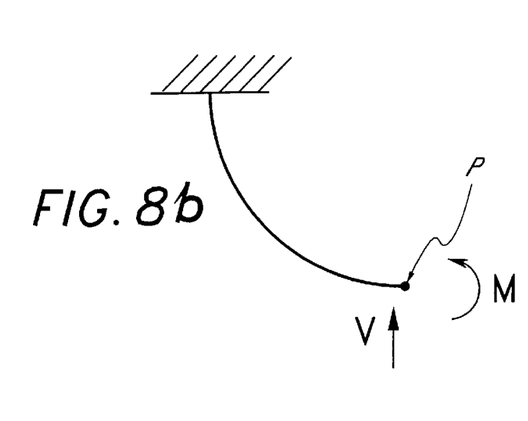
FIG. 8b is a schematic drawing of the curvilinear section of the ankle showing the applied forces and moments.
Figure 8C:
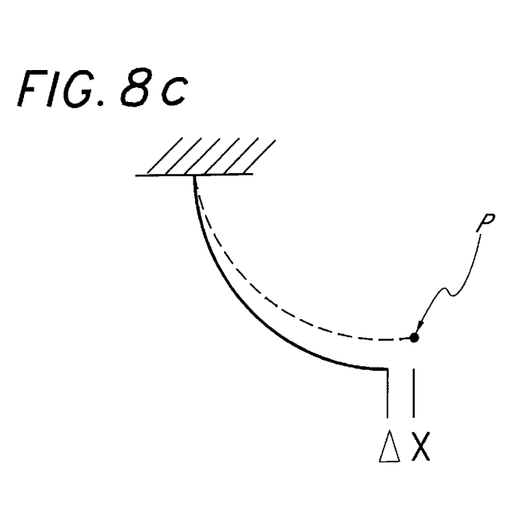
FIG. 8c is a schematic drawing of the ankle section showing the resultant horizontal deflection $\Delta x$.

As can be shown mathematically, a curved member having a certain radius of curvature deflects both vertically and horizontally when a vertical load is placed at the end of the curved member. For instance, as an upward force is directed at the toe end of the curved member, as schematically shown in FIGS. 8a–c, the toe member will deflect upward, causing a corresponding horizontal deflection in the forward direction $\Delta x$. As can be seen in FIG. 8c, there is both a vertical deflection component and a horizontal deflection component, $\Delta x$, which results from an upward force directed at the toe end of the curved member.

Though schematically the vertical deflection results in a forward horizontal deflection component, shown as $\Delta x$ in FIG. 8c, in actual practice this forward horizontal deflection results in a rearward horizontal movement relative to point P. In other words, when an amputee places a load on the toe section 28, the toe section becomes planted and the back end of the prosthesis, rather than the toe section, moves. As a result, when an amputee places weight at the toe end of the prosthesis, the horizontal deflection component is backward relative to the toe plant, rather than forward. In practical terms, what this means is that with every step taken, as the amputee plants the toe to push off, the toe section deflects upward, causing a corresponding horizontal deflection component which moves the prosthesis, and therefore the amputee, backward relative to the toe plant. As will be discussed, this rearward horizontal movement can cause the amputee to lose his or her balance, and make it difficult to control the prosthesis.

Thus, an important aspect of the present invention is the reduction in this horizontal movement or deflection component in the fore and aft direction as the amputee plants the toe. The prosthetic device 20 of the present invention reduces this horizontal deflection component, thereby serving to stabilize the amputee and provide a more natural feel. By reducing the backward movement of the prosthesis with every step taken, the amputee will not experience the destabilizing springiness associated with some prior prosthetic devices having large ankle radius sections.

It is important to note here that for active amputees, a large radius ankle section may be more desirable due to its ability to store additional energy and provide a better energy response. However, in view of the fact that many amputees are not generally very active, a prosthesis having improved control performance may be more desirable. Thus, the present invention represents a substantial improvement in the area of prosthetic devices to provide the amputee with increased control, which will help the amputee build confidence in the prosthetic device, resulting in improved adaptability and recovery.

This reduction in the horizontal deflection component, which can be provided by reducing the radius of curvature of the ankle section, can be shown mathematically. Test results will also show a dramatic difference in the amount of horizontal deflection caused by prosthetic devices having ankle sections of varying radii of curvature.

First of all, the amount of horizontal deflection caused relative to vertical deflection can be computed mathematically. Referring to FIG. 8a, an experimental ankle loading situation is schematically shown. A leg member 50 having an upper substantially vertical section 52, an intermediate curvilinear section 54 and a lower substantially horizontal section 56 is fixed at a point 58 at an upper end. An upward force F is applied at the toe end of the leg 50 at point T to simulate a toe push-off of the leg in normal walking or running. Assuming that the upper portion 52 is a substantially rigid member resistant to bending, FIG. 8b is a force/moment diagram for the curvilinear section 54. The upper end will be designated as fixed, as the upper portion 52 is substantially rigid. The lower end at point P will experience an upward force F (or a shear force V in FIG. 8b) and a moment M equaling the force F times the distance L minus r, which is the distance of 56 from the bottom end of the curvilinear section 54 to the application of force F.

From the reference "Formulas for Stress and Strain," R. J. Roark, 4th Ed., p. 180, the following formula is obtained to determine the amount of horizontal deflection relative to vertical deflection caused along the curved ankle section 54 by the upward force F:

$$\Delta X = \frac{1}{EI}\left[MR^2(1 - \theta\sin\theta\cos\theta) + VR^3\left(\frac{1}{2} - \cos\theta + \theta\sin\theta\cos\theta + \frac{\cos^2\theta}{2} - \sin^2\theta\right)\right]$$

ΔX—Movement in the horizontal direction of the Point P in FIGS. 8b and 8c
E—Modulus of Elasticity
I—Moment of Inertia
M—Applied Moment
V—Vertical Shear Load
R—Radius
θ—Included Angle of Radius in Radians

EXAMPLE 1

For a prosthetic device of the present invention having a 2-inch radius ankle section and a 0.24 inch constant thickness:

$E=20\ E^6$ lb/in$^2$
$t=0.24$ in
$I=bh^3/12=(2(0.24)^3)/12=0.0023$ in$^4$
$R=2$ in
$\theta=1.5708$ radians
$\sin\theta=1$
$\cos\theta=0$
$L=8$ in.

Given that the applied load F=150 lb, which is an average weight of an amputee, then the vertical shear load V=150 lb. and the applied moment M=150 (8−2)=900 in. lb.

$$\Delta X_1 = \frac{1}{20E6(.0023)}\ [(-900)(2)^2(1 - 1.5708(1) - 0) +$$
$$(-150)(2)^3(.5 - 0 + 0 + 0 - 1^2)]$$

$\Delta X_1 = 0.058$ in.

This is the horizontal deflection at point P caused by vertical load F. Because the toe section 56 is horizontal, little or no additional horizontal deflection will occur along the length of the toe section between point P and point T. Further, because the horizontal toe section 56 extends beyond point P, vertical deflection at point T will be greater, although the horizontal deflection will remain virtually unchanged. Thus, the relative horizontal deflection of the prosthesis caused by a vertically upward force is approximately 0.058 in. What this means is that with every step taken, the prosthetic device will move backward a distance of 0.058 inches with every 150-pound load placed on the toe.

EXAMPLE 2

For a prosthetic device of the prior art having a 5-inch radius ankle section, as shown in FIG. 6, and 0.24-inch constant thickness:

$E=20\ E^6$ lb/in$^2$
$t=0.24$ in
$I=bh^3/12=(2(0.24)^3)/12=0.0023$ in$^4$
$R=5$ in
$\theta=1.5708$ radians
$\sin\theta=1$
$\cos\theta=0$
$F=150$ lb
$M=150\ (8-5)=450$ in. lb.

$$\Delta X_2 = \frac{1}{20\ E^6\ (.0023)}\ [(-450)(5)^2(1 - 1.5708(1) - 0) +$$
$$(-150)(5)^3(.5 - 0 + 0 + 0 - 1^2)]$$

$\Delta X_2 = 0.343$ in.

This is the horizontal deflection at point P caused by vertical load F. Again, little or no further horizontal deflection will occur along the horizontal toe section 56. Thus, 0.343 inches represents the amount of horizontal deflection caused by a 150-pound upward force at the toe section of the prosthesis. What this means is that with every step taken, the amputee will experience a counteracting backward movement of approximately 0.34 inches as the amputee plants the toe of the prosthesis.

The results of these examples clearly show that the smaller radius ankle section of the present invention will result in much less horizontal deflection than the larger radius ankle sections of the prior devices. Indeed, comparing a 2-inch radius with a 5-inch radius shows that the 5-inch radius ankle section experiences approximately six times greater horizontal deflection than a 2-inch radius ankle section. This clearly shows that the present invention not only concentrates bending in the ankle section, but also prevents undesirable horizontal deflection which will cause the amputee to feel as though the prosthetic device were shifting slightly backward with each step. The present invention minimizes this horizontal deflection, which helps the amputee maintain greater control and stability during utilization of the prosthetic device.

The results of the foregoing examples are also based on ankle sections of constant thickness. The tapered ankle section 26 of the present invention would in fact further decrease the amount of horizontal deflection experienced. This is due to the fact that the more flexible lower portion, as will be discussed, of the ankle section 26 will experience more of the bending as opposed to further up on the ankle section. Thus, as the bending is concentrated lower in the ankle portion by the tapered construction, the horizontal movement will correspondingly decrease.

Figure 9A:
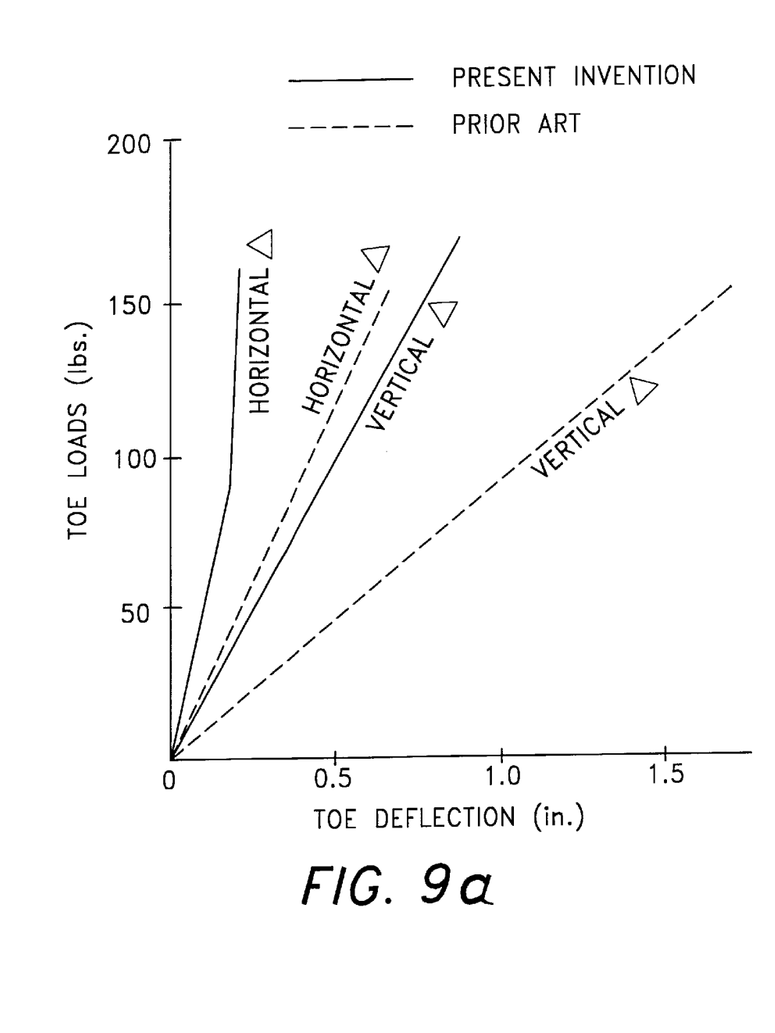
FIG. 9a is a chart showing horizontal and vertical deflections of the present invention and a prior device.
Figure 9B:
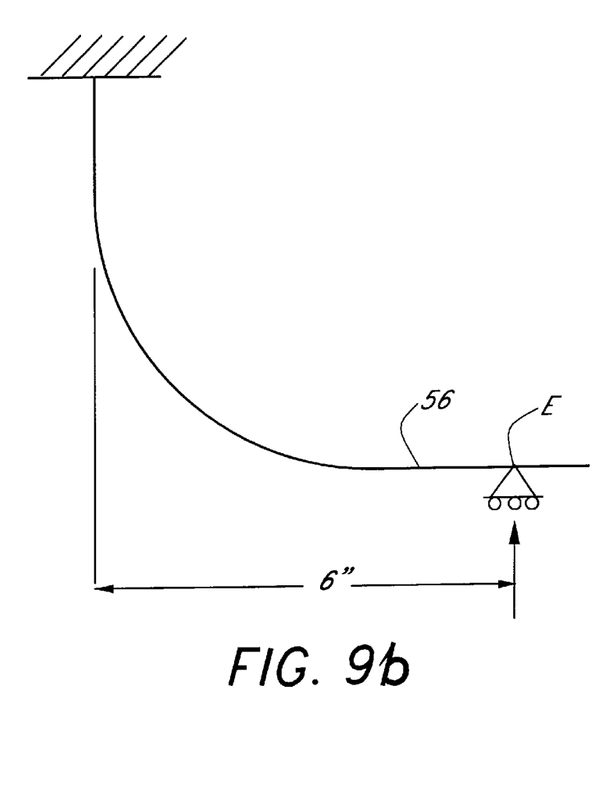

A test was also conducted on a prototype of the present invention and on a prior device having approximately a 5-inch radius ankle section to determine the actual vertical and horizontal deflections experienced at a point E, as shown in FIGS. 9a and b. The devices were tested under a standard loading machine with the upper end fixedly mounted. The load was imposed in an upward direction at point E, which was selected to be positioned about six inches horizontally from the vertical position of the ankle member. The load was up to and including a 150-pound load. This upward load was connected to a roller to permit horizontal movement at point E as the upward force was applied.

FIG. 9a charts the amount of deflection both horizontally and vertically from 0 load to 150-pound load. The results of the experiment were fairly dramatic. The amount of vertical and horizontal deflection of the present invention is shown in the solid lines, and the amount of vertical and horizontal deflection of the prior device is shown in the dashed lines. The vertical deflection of the present invention, given a 150-pound load at point E, was approximately 0.9 inches, while the amount of horizontal deflection caused by the same load was only approximately 0.2 inches. On the other hand, the vertical and horizontal deflection caused by a 150-pound load applied at point E on the prior device was significantly greater. The amount of vertical deflection, represented by a dashed line in FIG. 9a, was approximately 1.7 inches, while the horizontal deflection was approximately 0.75 inches. These results show that the prior device moves horizontally almost as much as the present invention moves vertically, given a 150-pound load.

This difference can also be described in terms of a ratio between the horizontal deflection and the vertical deflection. Given a 150-pound load, the ratio of horizontal deflection to vertical deflection of the present invention is a fraction of 0.2/0.9 or 0.22. The ratio of horizontal deflection to vertical deflection experienced by the prior device is a fraction of 0.75/1.7, which is approximately 0.44. This ratio is significant when considering that with every step taken, the vertical deflection of the toe section will result in a corresponding rearward horizontal deflection amounting to some fraction of the vertical deflection. Given a 0.44 ratio, the prosthetic device will move backward horizontally approximately 0.44 inches with every inch of vertical deflection experienced. Conversely, in the present invention, the amount of horizontal rearward deflection will be only approximately 0.22 inches with every inch of vertical deflection experienced.

Several factors contribute to this improvement in the ratio of horizontal deflection relative to vertical deflection. As is known in the art, and as can be shown mathematically, the ratio of horizontal deflection to vertical deflection at point P, as shown in FIG. 8c, will be nearly a constant ratio of approximately 0.59. Of course, this depends on whether the curve follows a single radius arc, and whether the curve extends along a 90° angle of radius. What causes the ratio of horizontal deflection to vertical deflection to decrease is a function of how tight the radius of curvature of the ankle section is and how long the toe section 56 extends forward from the ankle section. Because the horizontal toe section 56 will experience little or no horizontal deflection as vertical deflection increases, a longer toe section 56 will allow additional vertical deflection without increasing horizontal deflection. By decreasing the radius of curvature of the ankle section, a longer toe section 56 can be extended from the bottom of the ankle section, resulting in the capacity to permit additional vertical deflection without increasing associated horizontal deflection. This phenomenon significantly decreases the ratio between the horizontal deflection and vertical deflection as loads increase.

Preferably, in the present invention, the horizontal deflection $\Delta X$ is no more than 0.25 inches, given a 150 lb load at point E, although up to 0.5 inches would be permissible. Also, preferably, the ratio of horizontal deflection to vertical deflection at point E (or T) is less than one-third, although a ratio of up to 0.5 would be acceptable. As discussed, this ratio is nearly constant (0.59) at point P, see FIG. 8a, whether the ankle section radius is large or small. However, the ratio at point T varies depending on how small the radius is and how long the toe section 56 is. With a small radius ankle section, the resultant toe section 56 will be longer, resulting in greater vertical deflection at point T without necessarily increasing horizontal deflection. The ratio will also vary depending on whether the thickness is tapered along the ankle and toe sections. The thinner the toe section 56, the greater the vertical deflection at point T will be, and consequently, the greater the energy storage will be, without increasing horizontal deflection along the ankle section.

Taper of the Ankle Section, Heel and Toe

As seen in FIG. 3, the foot portion 24 has a tapered thickness, the taper being a function of the flexibility in the foot portion. Though the upper vertical section 30 is substantially uniform in thickness, the ankle section 26 has a thickness which is tapered from the upper part "a" through the middle part "b" to the lower part "c" of the curved section.

Preferably, a series of standard thicknesses are provided for amputees of varying sizes. For example, the prosthetic device 20 of the present invention may be provided in nine sizes with the designation "A1" through "A9," "A1" being the thinnest for the smallest amputee and "A9" being the thickest for a larger amputee. The following Table 1 gives thicknesses "t" at points "a," "b" and "c," corresponding to the upper, middle and lower portions of the ankle portion 26 for the nine size categories. Furthermore, Table 1 provides the area moment of inertia "I" about the bending axis for the points "a," "b" and "c" based on a foot portion 24 width of 2 inches.

TABLE 1

Tapered Ankle Section Thickness and Moment of Inertia

| | $t_a$, in | $t_b$, in | $t_c$, in | $I_a$, in$^4$ | $I_b$, in$^4$ | $100 (I_b/I_a)$ | $I_c$, in$^4$ | $100 (I_c/I_a)$ |
|---|---|---|---|---|---|---|---|---|
| A1 | .310 | .250 | .217 | .00500 | .00260 | 52.0 | .00170 | 34.0 |
| A2 | .321 | .261 | .226 | .00551 | .00296 | 53.7 | .00192 | 34.8 |
| A3 | .334 | .269 | .233 | .00621 | .00324 | 52.2 | .00211 | 34.0 |
| A4 | .347 | .278 | .241 | .00696 | .00358 | 51.4 | .00233 | 33.4 |
| A5 | .365 | .292 | .253 | .00810 | .00415 | 51.2 | .00270 | 33.3 |
| A6 | .386 | .307 | .266 | .00959 | .00482 | 50.3 | .00314 | 32.7 |
| A7 | .407 | .322 | .278 | .0112 | .00556 | 49.6 | .00358 | 32.0 |
| A8 | .428 | .338 | .292 | .0131 | .00644 | 49.2 | .00415 | 31.7 |
| A9 | .449 | .353 | .305 | .0151 | .00733 | 48.5 | .00473 | 31.3 |

As can be seen from Table 1, the thickness at the lower point "c" of the ankle section 26 is approximately 70% of the thickness at the upper part "a" for the sizes "A1" through "A9." Due to the area moment of inertia being proportional to the cube of the thickness at any one point, however, the area moment of inertia of $I_c$ in the lower region of the ankle 26 is between 31% and 35% of the area moment of inertia $I_a$. Also, the area moment of inertia $I_b$ at the middle section is between 48% and 54% of the area moment of inertia $I_a$ at the upper region "a." Due to the fact that the amount of deflection from a particular applied force is inversely proportional to the area moment of inertia, a majority of the deflection from bending of the prosthetic device 20 will occur in the lower portion of the ankle section 26, and more particularly, below the middle region "b" of the ankle section.

Because the upper part "a" of the curved section 26 is thicker than the lower part "c", most of the bending occurs along the lower third to lower one-half of the curved section. This further isolates the bending about the ankle region 26, and lowers the bending point. The stiffer upper part "a" of the curved section 26 also imparts a slightly greater resistance to bending, extending somewhat downwardly the stiffness of the pylon member 22 and the vertically aligned upper section 30.

As noted above, the flex characteristics of the toe and heel sections of a prosthetic foot are also important parameters in determining its overall performance. In addition to the lever arm or length of these members, their thickness or taper, of course, will also affect their flex characteristics. Thus making the lower part "c" of the curved ankle section 26 thinner and extending the taper along the toe section 28, additional flexibility can be imparted to the toe end 46 of the prosthesis. Indeed, in the preferred embodiment, the toe end 46 has a thickness which is approximately one-third to one-half of the thickness of the vertically aligned upper section 30 of the foot portion 24.

The heel portion 40 is also made relatively thinner than the vertically aligned upper section 30 of the foot portion 24, so as to impart flexibility to the heel area. A taper can also be provided in the heel portion 40, wherein the front end 40a of the heel portion which is connected to the underside of the foot portion 24 is slightly thicker than the rearward end 40b of the heel portion.

Though in the preferred embodiment each of these members are tapered, as shown in FIG. 1, many of the advantages of the present invention can be obtained utilizing a number of varying thicknesses, including a constant thickness throughout the foot portion 24 and heel portion 40. However, tapering of these members provides additional "feel" to the foot prosthesis 20, which would otherwise be absent without such tapering.

The toe section 28 and heel portion 40 are thinner, and thus are relatively more flexible than the ankle section 26 and the vertically aligned upper section 30. This flexibility is provided to more closely resemble the flexibility of movement found in the human foot. In the human foot, a number of joints are located which allow the foot to move in various directions. For instance, the metatarsal is joined such that the front end of the foot can move with respect to the remainder of the foot. By making the front end of the foot prosthesis thinner, additional flexibility is imparted so as to more closely resemble the flexibility of the human foot.

The width of the foot portion 24 can also vary, although in the preferred embodiment, the width is uniformly approximately 2 inches. The foot portion 24 and heel portion 40 can also be tapered in width, as well as thickness, to provide additional resistance or flexibility about various axes. For instance, by making the foot portion 24 slightly less wide along the vertically extending upper section 30, additional torsional flexibility can be provided.

Operation

In use, the foot prosthesis 20 of the present invention performs quite adequately and mimics the movement of a natural human limb. The design of the present invention simulates ankle motion that is smooth and continuous from heel-strike to toe-off. At heel-strike, the load exerted on the prosthetic device depresses the heel 40, which acts as a lever to plantarflex the toe 28. With the amputee's weight still behind the prosthetic device, the ankle section 26 bends backward, opening its radius of curvature. The natural tendency of the heel portion 40 and ankle section 26 to return to original flex positions helps shift the weight of the amputee forward to midstance. As the amputee rolls over from midstance to toe-load, the prosthesis 20 dorsiflexes, bending the ankle section 26 forward, causing the radius of curvature to close relative to the 90° position. At toe load, the amputee's weight is shifted forward, causing the toe section 28 to bend. With the toe section 28 bent, the prosthesis assumes a forwardly angled position, from which the natural tendency of the ankle section 26 to return to its original position causes the amputee to move forward as the energy is released at toe-off. By making the toe section 28 relatively flexible, the combination of the toe's flexibility with the energy being released from the ankle section 26 causes the amputee to move forward, rather than to an upright position.

Thus, the present invention provides a unique combination of prosthetic elements which perform much like a normal ankle joint, wherein the leg and shin portion are relatively stiff, and most of the bending takes place in a low, confined ankle region and a flexible toe and heel section. In addition, the present invention provides improved control and stability not previously provided by prior devices, as it reduces excessive horizontal movement and confines bending in a tight ankle section. Though those particular advantages are embodied in the invention as described herein, the invention is not intended to be limited to just the particular embodiment discussed. The invention also contemplates other embodiments which provide the advantages heretofore discussed.

What is claimed is:

1. A lower limb prosthesis for providing resilient kinematic support to an amputee relative to a ground surface, comprising:
   a pylon member having an upper end and a lower end, said lower end sized to be in the range of about 2½" to about 5" from said ground surface when said prosthesis is in use, said pylon member being substantially rigid along substantially its entire length; and a flexible foot member being monolithically formed of superimposed laminates of resin-impregnated filamentary material, said foot member comprising:

an upper attachment section rigidly attaching said foot member to said lower end of said pylon member, said upper attachment section being substantially rigid along its length and substantially vertically aligned along substantially its entire length;

a toe section being substantially flexible along its length and defining a lever arm having a length of about 4½", said toe section being substantially horizontally aligned along substantially its entire length such that said upper attachment section and said toe section are at approximately a 90° angle with one another; and an ankle section joining said upper attachment section and said toe section in a smoothly curving manner from said upper attachment section curving forwardly to said toe section, said ankle section having a radius of curvature of between 1½" and 3";

said ankle section and said toe section together comprising a curved cantilevered flexing member curving downward from adjacent said attachment section and forward through said toe section, said flexing member providing substantially the sole means of energy storage and return for said foot member and whereby said flexing member is sized and configured such that the component of horizontal deflection at a point adjacent the tip of said toe section is less than about one-third of the component of vertical deflection at said point in response to an upward force directed at said point.

2. The lower limb prosthesis of claim 1, further comprising an attachment device mounted on said upper attachment section, said attachment device comprising means for adapting said pylon member to an upper portion of said upper attachment section.

3. The lower limb prosthesis of claim 2, wherein said pylon member is tubular and said upper attachment section is substantially planar, said attachment device providing means for adapting said tubular pylon member to said planar upper attachment section.

4. The lower limb prosthesis of claim 1, further comprising a heel section extending rearwardly from adjacent said ankle section.

5. The lower limb prosthesis of claim 4, wherein said heel section is configured to be selectively attached and detached to a point between said ankle section and said toe section.

6. The lower limb prosthesis of claim 1, wherein said radius of curvature of said ankle section is about 2" defining a bending axis.

7. The lower limb prosthesis of claim 6, wherein said bending axis is positioned to be located no more than about 3.5" above said ground surface.

8. The lower limb prosthesis of claim 1, wherein said curved flexing member is tapered from said ankle section to said toe section, wherein substantially uniform stress distribution is obtained.

9. The lower limb prosthesis of claim 1, wherein said foot member is configured to be selectively attached and detached to a tubular pylon.

10. The lower limb prosthesis of claim 9, wherein an attachment member is secured to a back side of said pylon relative to a forward direction for said amputee, said attachment member having a vertically aligned attachment surface thereon for receiving said foot member.

11. The lower limb prosthesis of claim 1, wherein said pylon member is a cylindrical pylon.

12. The lower limb prosthesis of claim 1, wherein said foot member is permanently attached to said pylon member.

13. The lower limb prosthesis of claim 1, wherein the thickness of said toe section is between approximately one-third to approximately one-half the thickness of said upper attachment section.

14. The lower limb prosthesis of claim 1, further comprising a heel section extending rearwardly from adjacent said ankle section and wherein the thickness of said heel section is thinner than the thickness of said upper attachment section.

15. The lower limb prosthesis of claim 14, wherein said toe section and said heel section are substantially flat and coplanar with one another.

* * * * *